(12) United States Patent
Bonnette et al.

(10) Patent No.: US 9,005,163 B2
(45) Date of Patent: Apr. 14, 2015

(54) BALLOON CATHETER WITH EXTERNAL DELIVERY TUBE

(75) Inventors: Michael J. Bonnette, Minneapolis, MN (US); Debra M. Kozak, Forest Lake, MN (US); Eric J. Thor, Arden Hills, MN (US); Richard R. Prather, St. Michael, MN (US)

(73) Assignee: Bayer Pharma Aktiengesellschaft, Berlin (DE)

( * ) Notice: Subject to any disclaimer, the term of this patent is extended or adjusted under 35 U.S.C. 154(b) by 0 days.

(21) Appl. No.: 13/813,221

(22) PCT Filed: Aug. 3, 2011

(86) PCT No.: PCT/US2011/046402
§ 371 (c)(1),
(2), (4) Date: Jan. 30, 2013

(87) PCT Pub. No.: WO2012/018899
PCT Pub. Date: Feb. 9, 2012

(65) Prior Publication Data
US 2013/0131594 A1 May 23, 2013

Related U.S. Application Data

(60) Provisional application No. 61/370,222, filed on Aug. 3, 2010.

(51) Int. Cl.
*A61M 29/00* (2006.01)
*A61M 25/10* (2013.01)
(Continued)

(52) U.S. Cl.
CPC ............... *A61M 25/10* (2013.01); *A61F 2/958* (2013.01); *A61M 25/1002* (2013.01);
(Continued)

(58) Field of Classification Search
CPC ............ A61M 25/10; A61M 25/1029; A61M 25/104; A61M 2025/1052; A61M 25/1011; A61M 25/102; A61M 16/0463

USPC ............... 604/96.01, 103.14, 509, 103.07, 604/103.02, 507

See application file for complete search history.

(56) References Cited

U.S. PATENT DOCUMENTS 3,981,299 A * 9/1976 Murray ........................ 604/43
4,824,436 A 4/1989 Wolinsky
(Continued)

FOREIGN PATENT DOCUMENTS

EP 0920882 6/1999
WO 9618427 6/1996
(Continued)

OTHER PUBLICATIONS

C. Herdeg et al., Paclitaxel: Chemotheraphy for Restenosis Prophylaxis? Experimental Investigations in vitro and in vivo. Interventional Cardiology. 2000.
(Continued)

*Primary Examiner* — Scott Medway
(74) *Attorney, Agent, or Firm* — David Schramm

(57) ABSTRACT

A balloon catheter having a shaft, a balloon, and an external delivery tube, as well as methods of use thereof. In one example, the balloon catheter is an agent delivery catheter including a catheter body extending between catheter proximal and distal portions. An inflatable balloon assembly is coupled with the catheter body. An agent delivery assembly, which is coupled with the catheter body and the inflatable balloon assembly, includes a delivery lumen extending through the catheter body and an agent delivery tube extending along an exterior balloon surface. The agent delivery tube includes at least one delivery orifice directed outside of the exterior balloon surface. The agent delivery assembly is isolated from fluid communication with the inflatable balloon assembly.

6 Claims, 9 Drawing Sheets

(51) Int. Cl.
*A61F 2/958* (2013.01)
*A61M 25/00* (2006.01)
(52) U.S. Cl.
CPC ........ *A61M 25/104* (2013.01); *A61M 25/0032* (2013.01); *A61M 25/0097* (2013.01); *A61M 25/1034* (2013.01); *A61M 25/1036* (2013.01); *A61M 2025/105* (2013.01); *A61M 2025/1086* (2013.01)

(56) References Cited

U.S. PATENT DOCUMENTS

| | | | |
|---|---|---|---|
| 5,254,089 A | | 10/1993 | Wang |
| 5,318,531 A * | | 6/1994 | Leone ............... 604/103.01 |
| 5,336,178 A * | | 8/1994 | Kaplan et al. ............ 604/509 |
| 5,342,301 A | | 8/1994 | Saab |
| 5,464,395 A | | 11/1995 | Faxon et al. |
| 5,558,642 A | | 9/1996 | Schweich, Jr. et al. |
| 5,562,620 A | | 10/1996 | Klein et al. |
| 5,653,689 A * | | 8/1997 | Buelna et al. .......... 604/103.09 |
| 5,674,287 A | | 10/1997 | Slepian et al. |
| 5,713,860 A | | 2/1998 | Kaplan et al. |
| 5,716,340 A | | 2/1998 | Schweich, Jr. et al. |
| 5,785,679 A * | | 7/1998 | Abolfathi et al. ........ 604/509 |
| 5,792,106 A | | 8/1998 | Mische |
| 5,810,767 A | | 9/1998 | Klein |
| 5,840,066 A | | 11/1998 | Matsuda et al. |
| 5,876,426 A | | 3/1999 | Kume et al. |
| 5,882,335 A * | | 3/1999 | Leone et al. ............ 604/103.02 |
| 5,902,266 A | | 5/1999 | Leone et al. |
| 6,053,900 A * | | 4/2000 | Brown et al. ............... 604/500 |
| 6,063,101 A | | 5/2000 | Jacobsen et al. |
| 6,129,706 A * | | 10/2000 | Janacek ................. 604/103.08 |
| 6,231,562 B1 * | | 5/2001 | Khosravi et al. ............ 604/507 |
| 6,398,757 B1 | | 6/2002 | Varenne et al. |
| 6,497,721 B2 * | | 12/2002 | Ginsburg et al. ............ 607/106 |
| 6,527,790 B2 | | 3/2003 | Chien et al. |
| 6,554,801 B1 | | 4/2003 | Steward et al. |
| 6,733,474 B2 | | 5/2004 | Kusleika |
| 8,439,890 B2 * | | 5/2013 | Beyar et al. .................. 604/507 |
| 8,585,959 B2 * | | 11/2013 | Burton ....................... 264/532 |
| 2004/0260239 A1 | | 12/2004 | Kusleika |
| 2006/0190022 A1 * | | 8/2006 | Beyar et al. .................. 606/192 |
| 2007/0078433 A1 | | 4/2007 | Schwager et al. |
| 2007/0250035 A1 | | 10/2007 | El-Nounou et al. |
| 2009/0105687 A1 | | 4/2009 | Deckman et al. |
| 2009/0112184 A1 | | 4/2009 | Fierens et al. |

FOREIGN PATENT DOCUMENTS

| | | |
|---|---|---|
| WO | 9717099 | 5/1997 |
| WO | 0119445 | 3/2001 |
| WO | 2008066610 | 6/2008 |
| WO | 2009066330 | 5/2009 |

OTHER PUBLICATIONS

C. Dommke, et al., Local paclitaxel delivery after coronary stenting in an experimental animal model. Throm Haemost, 98, pp. 674-680. 2007. Schattauer GmbH, Suttgard.

C. Herdeg, et al., Successful Local Antiproliferative paclitaxel delivery in a repeatedly restenosed lesion of the right coronary artery after drug eluting-stent implantation. Clin Res Cardiol 97:46-52. 2008.

GENIE by Acrostak., A non-traumatic local drug delivery catheter to treat stenosis., Acrostak.

Herdeg, et al., GENIE catheter for liquid local drug delivery. EuroIntervention. 2007;3:286-288.

The the International Search Report, International Preliminary Report on Patentability and Written Opinion from corresponding PCT Application No. PCT/US2011/046402.

Efficiency of a New Therapy to Treat Stenosis of Coronary Vessels in Comparison With Two Already Admitted Therapies. Clinical Trial. University Hopsital Tuebingen. (http://clinicaltrials.gov/ct2/show/NCT00396929).

* cited by examiner

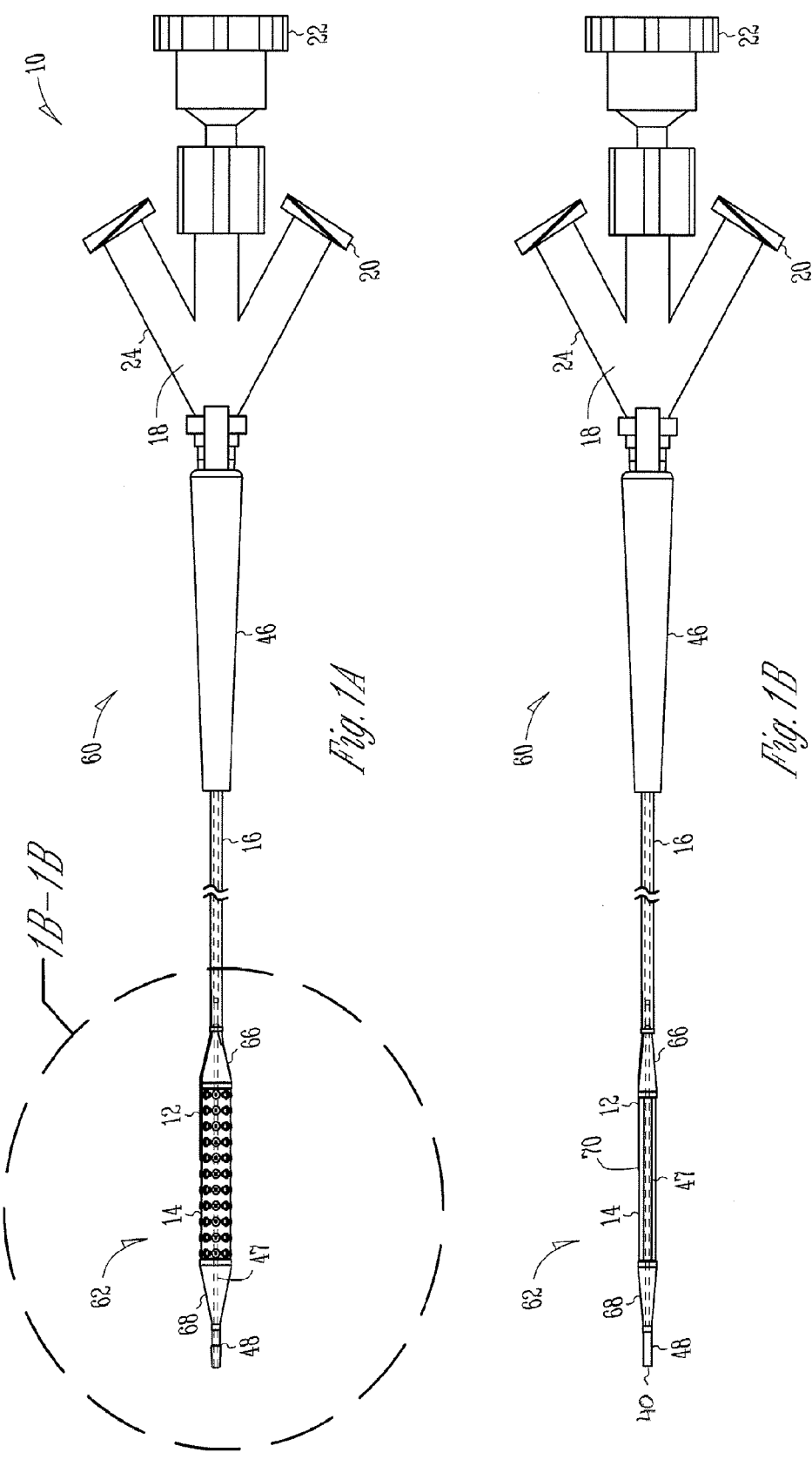

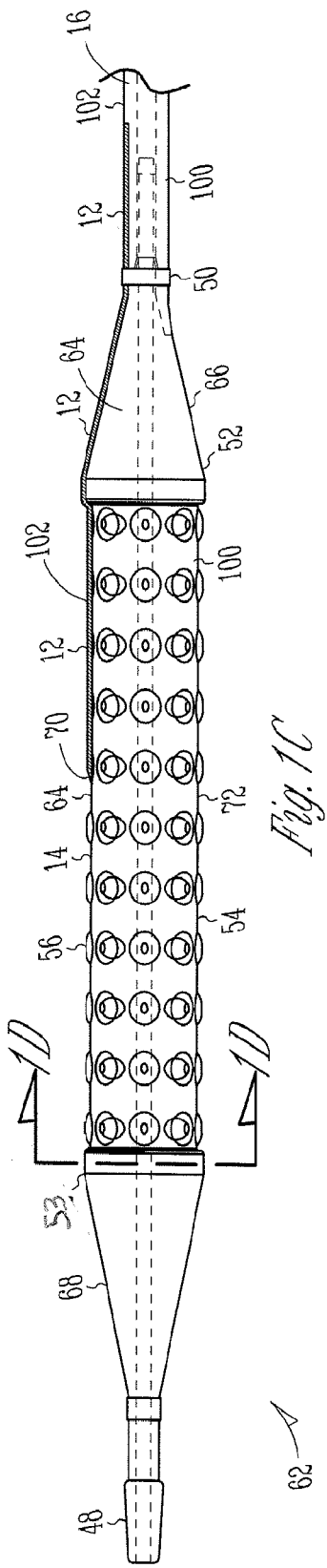
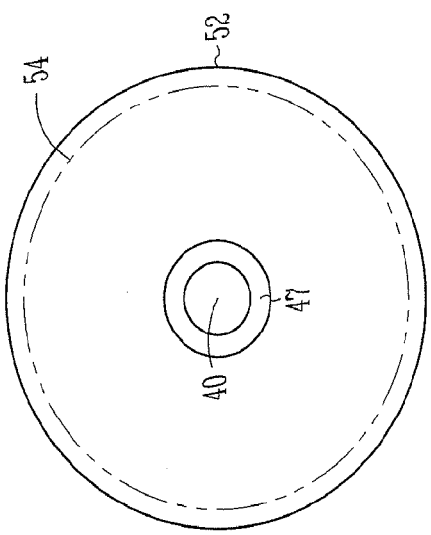

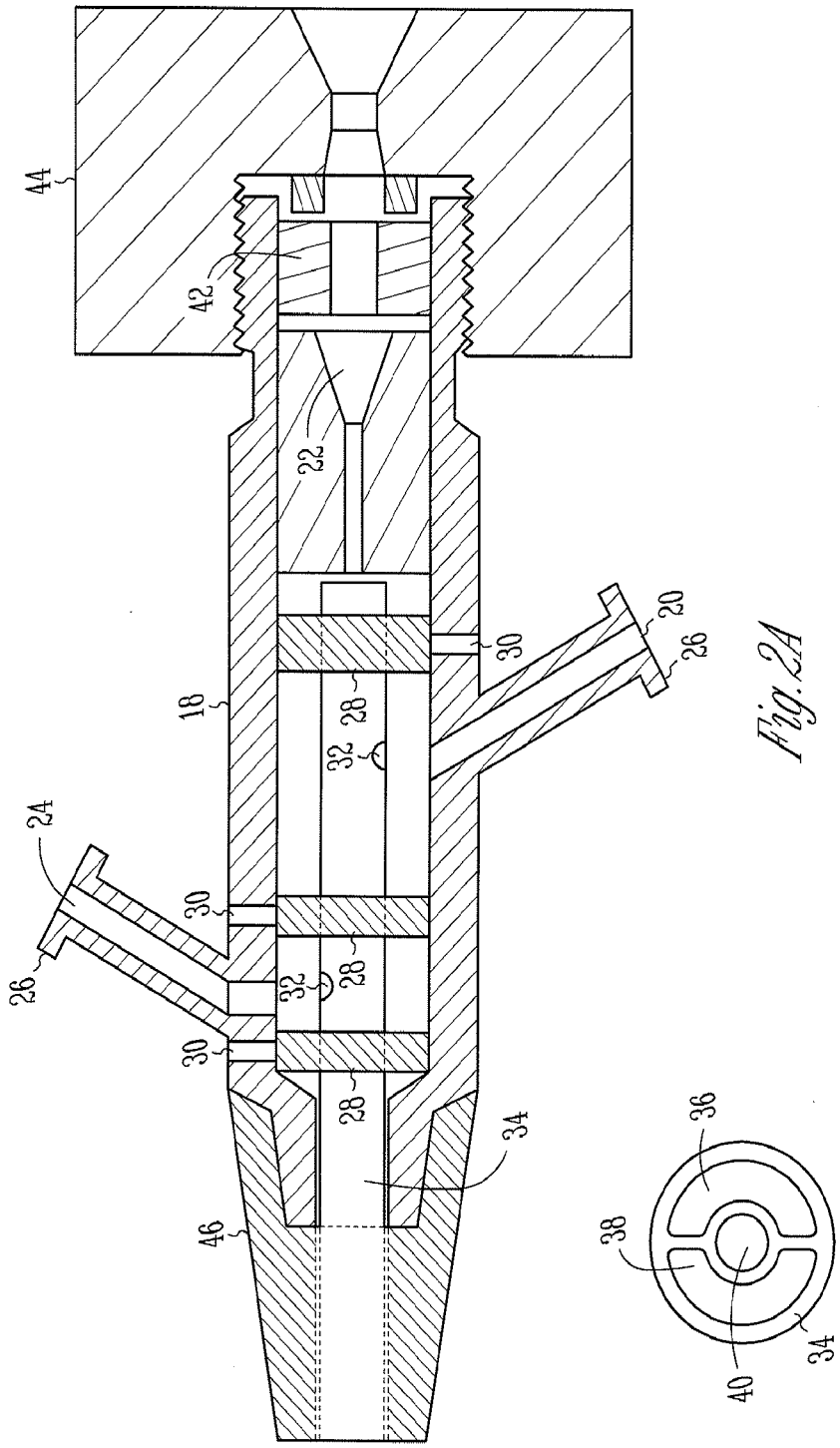

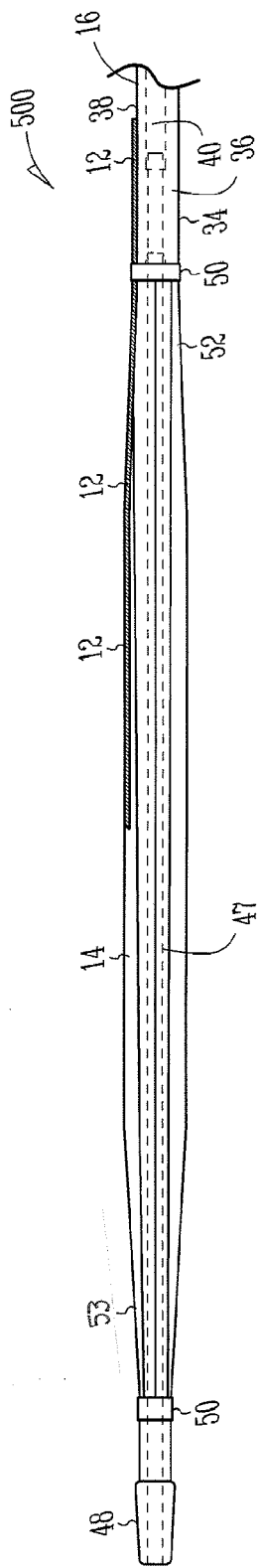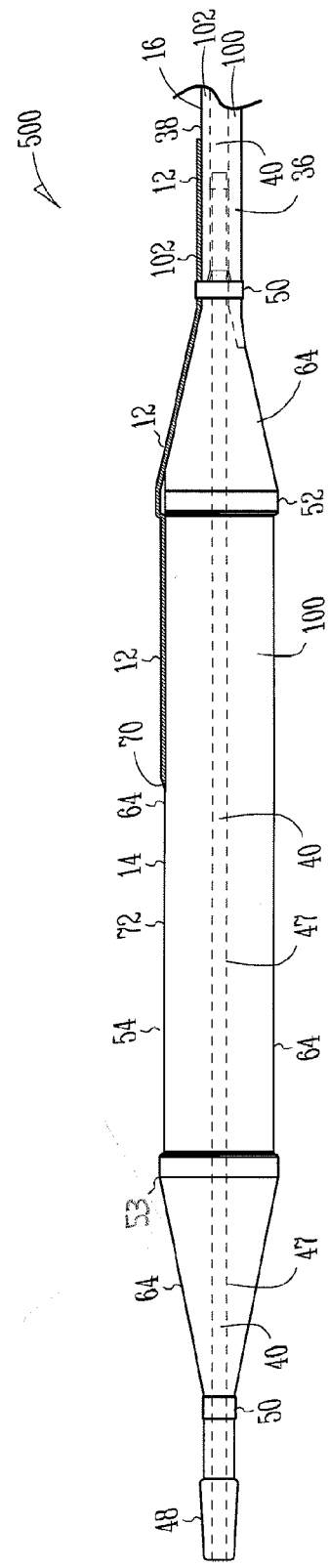

BALLOON CATHETER WITH EXTERNAL DELIVERY TUBE

CROSS-REFERENCE TO RELATED APPLICATIONS

This application is the U.S. National Phase of International Patent Application No. PCT/US2011/046402, filed Aug. 3, 2011, which claims priority to U.S. Provisional Patent Application No. 61/370,222, filed Aug. 3, 2010, the disclosures of which are incorporated herein by reference in their entirety.

FIELD OF THE DISCLOSURE

Embodiments of the present disclosure generally relate to a balloon catheter having an external delivery tube.

BACKGROUND

The delivery of therapeutic agents to the inner lining of vessel walls can be very effective to address various types of vascular injury. A key consideration for such procedures is the precise delivery of a predetermined amount of therapeutic agent. Some methods of delivery present challenging manufacturing processes in order to control the amount of therapeutic agent on the delivery device. For example, dip coated catheter balloons (percutaneous transluminal angioplasty (PTA) catheter balloons) can present several drawbacks during manufacturing. Application of a uniform coating can be difficult when using the dipping process as the process may be very labor intensive and time consuming.

Further, in other devices fluids are metered through weeping orifices within an inflatable balloon to provided localized delivery of the fluid (e.g., therapeutic agents or contrast media). This configuration requires filling the inflatable balloon with the infused fluid. In some examples, the infused fluid is a toxic substance with localized therapeutic benefits to the vessel. It is difficult to meter the flow of the infused fluid through weeping orifices that expand and contract to some degree with deployment and storage of the balloon through inflation. For example, a specified pressure must be maintained to inflate the balloon. The specified pressure for inflation may administer the infused fluid at too great a flow rate to the vessel with attendant risks (e.g., overdosing of the infused fluid, delivery of supplemental infused fluid downstream from the desired treatment site and the like).

Additionally, with smaller weeping orifices the infused fluid may plug the orifices and prevent the precise delivery of the desired dose of the fluid. Further still, where expensive agents, such as pharmaceuticals, are used it is expensive to use the agent as the media for inflation of a balloon, a relatively large volume, as compared to the small volume of agent required for delivery to the desired treatment location. The volume of agent used to inflate the balloon is often not recoverable thereby greatly enhancing the cost of the procedure.

SUMMARY

In general, various embodiments of the present disclosure are directed to a balloon catheter having an external delivery tube. In one embodiment, a catheter (e.g., a catheter body) having at least a balloon, a catheter shaft, and a delivery tube extending over at least a portion of the balloon is disclosed.

In various embodiments, a catheter having a connector assembly with an inflation channel, a guidewire channel, and a delivery channel; a strain relief connected at a proximal end to a distal end of the connector assembly; a catheter shaft connected at a proximal end to a distal end of the strain relief; a trilumen tube extending from the connector assembly to a distal end of the catheter shaft and having an inflation lumen that is in fluid communication with the inflation channel, a guidewire lumen configured for disposition of a guidewire therein and in fluid communication with the guidewire channel, and a delivery lumen in fluid communication with the delivery channel; a delivery tube in fluid communication with the delivery lumen at the distal end of the catheter shaft; a stem portion connected at a proximal end to the distal end of the catheter shaft and having a stem guidewire lumen configured for disposition of the guidewire therein and in fluid communication with the guidewire lumen; a tip connected at a proximal end to a distal end of the stem portion and having a tip guidewire lumen configured for disposition of the guidewire therein and in fluid communication with the stem guidewire lumen; and an inflatable balloon (part of an inflatable balloon assembly) positioned substantially around the exterior of the stem portion, having proximal and distal ends, and in fluid communication with the inflation lumen, wherein the delivery tube extends over at least a portion of the inflatable balloon is disclosed.

Methods of delivering a therapeutic or other solution to a target site using the catheter having an external delivery tube set forth herein are also disclosed.

Those and other details, objects, and advantages of the present disclosure will become better understood or apparent from the following description and drawings showing embodiments thereof.

BRIEF DESCRIPTION OF THE DRAWINGS

The accompanying drawings illustrate examples of embodiments of the disclosure. In such drawings:

FIGS. 1A-1C show diagrams of embodiments of an agent delivery catheter (e.g., a balloon catheter):

FIG. 1A is a side view of one example of an agent delivery catheter with an inflatable balloon in a deployed configuration, the agent delivery catheter having an external delivery tube.

FIG. 1B is a detailed side view of the agent delivery catheter of FIG. 1A with the inflatable balloon in a stored configuration.

FIG. 1C is a detailed side view of the agent delivery catheter of FIG. 1A with an enlarged view of the distal end showing the balloon of an inflatable balloon assembly in a deployed configuration and the external delivery tube is positioned along the deployed inflatable balloon.

FIG. 1D is a cross-sectional view taken along line 1D-1D in FIG. 1C of one example of an inflatable balloon having proximal and distal shoulders creating a well.

FIG. 2A is a cross-sectional view of an embodiment of a connector assembly (a manifold assembly) for use with a balloon catheter having an external delivery tube (an agent delivery catheter).

FIG. 2B is a detailed cross-sectional view showing a trilumen tube used with the balloon catheter having an external delivery tube.

FIG. 5A is a detailed side view of another example of an agent delivery catheter with an inflatable balloon in a stored configuration.

FIG. 5B is a detailed side view of the agent delivery catheter of FIG. 4A showing the balloon of an inflatable balloon assembly in a deployed configuration and the external delivery tube is positioned along the deployed inflatable balloon.

DESCRIPTION

Figure 3A:
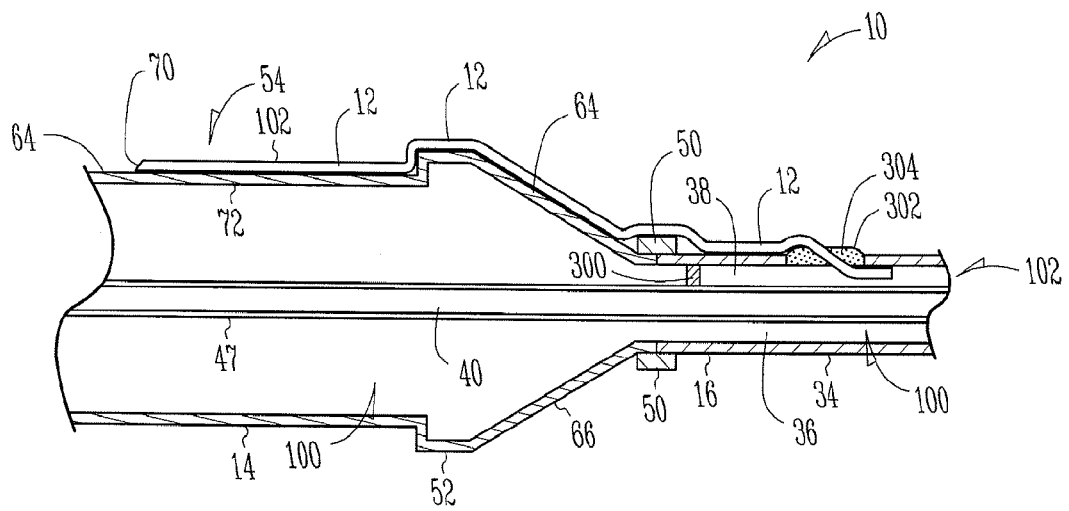
FIG. 3A is a cross-sectional view of a portion of trilumen tube used with the balloon catheter along a bisecting plane of the agent delivery catheter shown in FIG. 1C.

In all of its embodiments, the present disclosure relates to an agent delivery catheter 10 (e.g., a balloon catheter), such as for example and without limitation a PTA catheter, having an external delivery tube 12. See FIGS. 1A and 1C. In one embodiment, the catheter 10 includes a balloon 14, a catheter shaft 16, and the delivery tube 12 extending over at least a portion of the balloon 14.

In another embodiment, the catheter 10 (e.g., a catheter body) has a manifold assembly 18 (e.g., a connector assembly configured to couple with one or more fluid sources and instruments) with an inflation channel 20, a guidewire channel 22, and a delivery channel 24. See FIGS. 1A and 2A. In an example, the inflation channel 20 and the delivery channel 24 may have a luer fitting 26 for connection to an instrument, such as a syringe, for example and without limitation, for disposal of solutions into the catheter 10. See FIG. 2A.

The channels 20, 22, and 24 of the manifold assembly 18 may be separated by adhesive 28, such as an epoxy or other hardenable material, that is added through adhesive openings 30 in the manifold assembly 18. In an example, a Teflon® rod stock is placed in one or more trilumen openings 32 of a trilumen tube 34 at the base of the inflation channel 20 and the delivery channel 24. Adhesive is then added and the rod stock is removed after the adhesive hardens to maintain the opening during construction. As shown, for instance in FIG. 2A, the adhesive 28 separates the channels 20, 22 and 24 and correspondingly separates the inflation lumen 36, the delivery lumen 38 and the guidewire lumen 40, as described in the further detail below. Stated another way the delivery and inflation systems (passages and features providing delivery of agents and inflation of a balloon) are entirely separated with the fluid from the delivery system isolated from the fluid of the inflation system. As described below, this provides several advantages including precise metering of an infused fluid while the balloon 14 is maintained at a desired pressure for deployment.

The trilumen tube 34 has an inflation lumen 36, a delivery lumen 38, and a guidewire lumen 40. See FIG. 2B. The trilumen tube 34, in one example, is extruded from, but not limited to, Pebax® resin, polyurethane, vestimid, or other similar materials. In an example, the inflation lumen 36 and the delivery lumen 38 are located on either side with the guidewire lumen 40 in the center. The inflation lumen 36 and the delivery lumen 38 are in separated fluid communication with the inflation channel 20 and the delivery channel 24, respectively, through the trilumen openings 32. See FIG. 2A. As described above, the inflation lumen 36 and the delivery lumen 38 provide separate passages that substantially prevent the intermingling of infused fluids in the delivery lumen 38 with the inflation fluids within the inflation lumen 36. That is to say, the infused fluids, such as an expensive high concentration therapeutic agent, are delivered solely through the delivery lumen 38 and are not used for inflation of the balloon 14 (e.g., the infused fluids are not delivered through the inflation lumen 36).

The guidewire lumen 40 is in fluid communication with the guidewire channel 22 and is configured for disposition of a guidewire (or other instrument) therein. The guidewire channel may have a guidewire seal 42, such as a deformable seal member used in a touhy fitting. The connector assembly 18 may also have a cap 44, such as a threaded or rotating cap.

The trilumen tube 34 runs through a strain relief fitting 46 connected at a proximal end to a distal end of the connector assembly 18 and at a distal end to a proximal end of a catheter shaft 16. See FIGS. 1A and 2A. The trilumen tube 34 continues through to a distal end of the catheter shaft 16. See FIGS. 1A-C. The delivery tube 12 (described in further detail below) is in fluid communication with the delivery lumen 38 of the trilumen tube 34 at the distal end of the catheter shaft 16. See FIGS. 1C and 2A. As discussed herein the catheter 10 (a catheter body including the catheter shaft 16 and in one example the manifold assembly 18) includes proximal and distal catheter portions 60, 62. In one example the catheter shaft 16 extends between the proximal and distal catheter portions 60, 62.

During manufacture, a stem portion 47 of the catheter 10 is connected at a proximal end to the distal end of the catheter shaft 16 (e.g., the trilumen tube 34) and has a stem guidewire lumen configured for disposition and sliding of the guidewire therein and in fluid communication with the guidewire lumen 40. See FIG. 1B. In one manufacturing example, the trilumen tube 34 is partially removed adjacent to the balloon 14 to leave the guidewire lumen 40 contained within the stem portion 47. Removal of the remainder of the trilumen tube 34 provides access to the balloon 14 and the delivery tube 12 for each of the inflation lumen 36 and the delivery lumen 38, respectively. For instance, the trilumen tube 34 is cut to expose the stem portion 47. In another manufacturing example, the stem portion is adhered, welded and the like to a distal portion of the trilumen tube 34 and is coupled to ensure fluid communication between the guidewire lumen 40 of the trilumen tube 34 and the stem guidewire lumen of the stem portion 47.

Optionally, a tip 48 is connected at a proximal end of the tip to a distal end (e.g., distal portion) of the stem portion 47 of the catheter 10 and has a tip guidewire lumen configured for disposition and sliding of the guidewire therein and in fluid communication with the stem guidewire lumen such that the guidewire may run through the entire length of the catheter 10 (e.g., the catheter body). In one example, the tip 48 is constructed with an atraumatic material or feature including, but not limited to, polyurethane, a coil, rubber and the like.

As shown in FIGS. 1A-C, an inflatable balloon 14 is positioned substantially around the exterior of the stem portion 47 (e.g., the trilumen tube 34), having proximal and distal ends, and is in fluid communication with the inflation lumen 36. The inflatable balloon 14 is part of an inflatable balloon assembly 100 including the inflation channel 20 and the inflation lumen 36 of the trilumen tube 34. As shown in FIG. 1C, marker bands 50 are provided at the proximal and distal balloon ends 66, 68 of the balloon 14. Optionally, the balloon 14 is coupled with the catheter shaft 16 at the proximal balloon end 66 with an adhesive, weld, heat bond or the like between the balloon and the catheter shaft 16. In another example, the balloon 14 is coupled with the stem portion 47 similarly at the distal balloon end 68. As discussed below, in one example, the balloon 14 is constructed of a first material and is coupled with the catheter shaft 16 constructed with a second material. For instance, the end of the balloon is coupled over top of the end of the catheter shaft 16.

The inflatable balloon 14, in one example is constructed with, but not limited to, non-compliant (but flexible) materials such as polyesters (e.g., polyethylene terephthalate (PET) or Dacron), Pebax® resin (available from Arkema, Inc.), nylon, blends of the same and the like. In another example, the inflatable balloon 14 is constructed with, but not limited to, compliant materials, such as polyethylene, silicone or latex. In still another example, the inflatable balloon 14 is constructed with, but not limited to, semi-compliant materials (capable of some amount of stretching relative to non-compliant materials), such as Pebax® resin, nylon, blends of the same and blends including polyesters.

As shown in FIG. 1C, the delivery tube 12, such as an agent delivery tube, extends over at least a portion of the inflatable balloon 14. For instance, the delivery tube 12 extends over an exterior balloon surface 64. The delivery tube 12 includes at least one agent delivery orifice 70 (for instance at the distal end of the delivery tube 12) directed outside of the exterior balloon surface. Stated another way, the delivery tube 12 extends along the exterior balloon surface 64 of the balloon 64 and provides at least one delivery orifice that is directed toward the exterior of the balloon, for instance between the balloon 14 and a vessel wall. As stated above with regard to the delivery lumen 38 and the delivery channel 24, the delivery tube 12 is similarly isolated from the balloon 14 (and the inflatable balloon assembly 100) to provide a dedicated delivery system for infusing agents without relying on the pressure and volume of the inflatable balloon 14. Stated another way, the delivery lumen 38, the delivery channel 24 and the delivery tube 12 form an agent delivery assembly 102 extending at least partially along the exterior balloon surface 64 that is fluidly separated from the inflatable balloon assembly 100. Optionally, the delivery tube 12 can extend along the interior surface of the exterior balloon surface 64. For instance, the delivery tube 12 extends at least partially through the inside of inflatable balloon 14 and penetrates through the balloon 14 so that delivery orifice 70 in on the exterior balloon surface 64.

The balloon catheter 10 may also have marker bands 50 at the proximal and distal ends of the inflatable balloon 14. In an example, the catheter shaft 16 may be constructed of trilumen Pebax® resin, the stem portion 47 may be constructed of polyimide, and the tip 48 may be constructed of molded Pebax® resin. In another example, the lumens 36, 38, and 40 of the trilumen tube 34 may comprise the catheter shaft 16, the stem portion 47, and the tip 48 as described above such that the guidewire lumen 40 extends through the length of the catheter 10.

Referring again to FIG. 1C, as disclosed herein, the delivery tube 12 (e.g., the agent delivery tube) may be a hollow body of any shape in its cross-section, for example and without limitation, cylindrical, square, elliptical, oval and the like. The delivery tube 12 may be constructed from any suitable material, for example and without limitation, Pebax® resin, nylon, polyethylene terephthalate (PET), polyurethane, polypropylene, polyethylene, etc. For instance, the delivery tube 12 is constructed with a 300 micron hollow fiber. In another example, the delivery tube 12 is an oxygenated fiber, such as microporous polypropylene tubing configured to allow an adhesive interposed between the delivery tube 12 and the balloon 14 to wick into the micropores.

The length of the delivery tube 12 is sized according to the balloon 14 in one example. In one embodiment, the delivery tube 12 has a small profile to minimize drug leakage at the vessel contact site. For instance, by providing a delivery tube 12 with a small profile, the balloon 14 is able to readily wrap around the delivery tube and engage with the vessel wall and substantially seal any openings between the delivery tube, the balloon 14 and the vessel wall. In another example, one or more of the balloon 14 and the delivery tube 12 are constructed with pliable materials that readily deform (while maintaining the delivery tube open for agent delivery) and provide a seal between the delivery tube 12 and the balloon 14. In yet another embodiment, the delivery tube 12 is incorporated into the sidewall of the balloon 14 and is thereby substantially flush or within the outer perimeter of the balloon 14 including the proximal shoulder 52.

In various embodiments the delivery tube 12 is secured into the delivery lumen 38 at the distal end of the catheter shaft 16. The delivery tube 12 may be secured, for example without limitation, by bonding, such as with cyanoacrylate, or heat welding. The delivery tube 12 may also be secured, for example by bonding, to the balloon 14 in at least one location. In one embodiment, at least the tip of the delivery tube 12 is secured to the balloon 14.

The delivery tube 12 may be used to deliver any therapeutic agent or other solution, such as, for example without limitation, saline. The therapeutic agent or other solution may be a liquid, dispersion, slurry, viscous fluid, etc. As used herein, "therapeutic agent" includes, but is not limited to, any therapeutic, for example drugs, genetic material, and biological material. Genetic material includes, for example and without limitation, DNA or RNA, viral vectors and non-viral vectors. Biological material includes, for example and without limitation, cells, bacteria, proteins such as growth factors, peptides, lipids, and hormones. Drugs include, for example and without limitation, anti-thrombogenic agents, anti-proliferative agents, anti-inflammatory agents, anti-neoplastic agents such as epothilone and its derivatives, antimiotic agents, anti-oxidants, anti-coagulants, immunosuppressants such as sirolimus and its derivatives, vascular cell growth promoters, vascular cell growth inhibitors, antibiotic agents, angiogenic substances, restenosis-inhibiting agents, and drugs for heart failure. The "therapeutic agent" may include a combination of one or more therapeutics. Particular embodiments include restenosis-inhibiting agents such as Taxol, paclitaxel, paclitaxel analogues, derivatives, and mixtures thereof, such as Abraxane® pharmaceutical composition (available from Abraxis Bioscience, Inc.). In an example, carriers may be used with the therapeutic, such as, for example and without limitation, bioabsorbable agents, fibrin glue, sugar, honey, microspheres, microtubes, and physiologically compatible non-reactive drug transfer, contrast, or radio opaque agents, such as urea, iopromide, iopamidol, cremophore EL, vitamin E, Tocopheryl Polyethylene Glycol Succinate (TPGS), etc. In an example, the therapeutic is a drug solution consisting of: 0.3 cc Tween® surfactant solution (0.1 cc Tween® surfactant added to 2 cc saline), 0.5 cc Fibrin (Tisseel® adhesive minus thrombin), 0.3 cc Isovue® contrast agent, and 5 cc Abraxane® pharmaceutical composition (5 mg/cc).

In various embodiments, the inflatable balloon 14 may have a proximal shoulder 52 and a distal shoulder 53 creating a well 54 for localized delivery of the therapeutic or other solution. See FIG. 1C. The delivery tube 12 extends over at least the proximal shoulder 52 or a portion of the balloon 14. In an example, the delivery tube 12 extends over the inflatable balloon 14 to about the proximal side of the distal shoulder 53. Stated another way, the at least one delivery orifice 70 of the delivery tube 12 is positioned proximal to the distal shoulder 53. In another example, the at least one delivery orifice 70 is interposed anywhere between the proximal and distal shoulders 52 and 53 (e.g., within the well 54). In yet another example, the delivery tube 12 includes a plurality of delivery orifices 70 along the delivery tube 12, such as perforations. The plurality of delivery orifices 70 are, in still another example, positioned along the portion of the delivery tube 12 within the well 54.

Referring again to FIG. 1C, and as previously discussed, the well 54 is positioned between the proximal and distal shoulders 52 and 53. The well 54 is formed by a well portion 72 of the exterior balloon surface 64 recessed relative to the proximal and distal shoulders 52 and 53 (e.g., the well portion 72 is recessed from the shoulders between around 0.1 and 1.5 millimeters). In one example, the well portion 72 is molded in the recessed configuration shown in FIG. 1C during construction of the balloon 14. The well 54 cooperates with the shoulders 52 and 53 to provide a closed volume in intimate contact with a vessel wall (e.g., a portion of the wall designated for treatment). The shoulders 52 and 53 provide proximal and distal interfaces with the vessel wall that occlude the volume and substantially prevent the flow of agent out of the volume of the well 54. That is to say, with inflation of the balloon 14, the shoulders 52 and 53 are engaged with the vessel wall to seal the balloon 14 at proximal and distal ends with the well 54 therebetween.

As discussed above, and shown in FIG. 1C, the delivery tube 12 extends over the shoulder 52 with the at least one delivery orifice 70 directed into the well 54. A relatively small volume of agent (e.g., a medicament and the like) is thereby delivered to the designated portion of the vessel wall and reliably retained in intimate contact with the vessel wall for a specified time according to inflation of the balloon 14. The catheter 10 is thereby able to deliver a low dose (small volume) of an agent with a high concentration to a specified location within the vessel and thereafter administer and retain the agent in close intimate contact with the vessel wall. Precise metering and dosing of the agent is thereby possible with the configuration shown having the closed well 54.

Referring now to FIG. 3A, a detailed view of the proximal balloon end 66 in the deployed configuration shown in FIG. 1C is provided. FIG. 3A shows one example of the delivery tube 12 extending along the balloon 14 from the trilumen tube 34 and into the well 54. The delivery orifice 70 is directed into the well 54 (e.g., outside of the exterior balloon surface 64. Proximal to the proximal balloon end 66, the trilumen tube 34 is shown with each of the lumens 36, 38, 40 extending proximally toward the balloon 14. The delivery lumen 38 includes a lumen seal 300 (an adhesive, plug or the like) positioned within the delivery lumen distal to a delivery interface port 302 (See also FIG. 3B) configured to couple the delivery tube 12 with the delivery lumen 38. The inflation lumen 36 opens into the balloon 14. In the example shown, the guidewire lumen 40 continues distally. As described above, in one example the guidewire lumen 40 is enclosed within the stem portion 47 (e.g., an exposed portion of the trilumen tube 38) extending through the balloon 14.

Figure 3B:
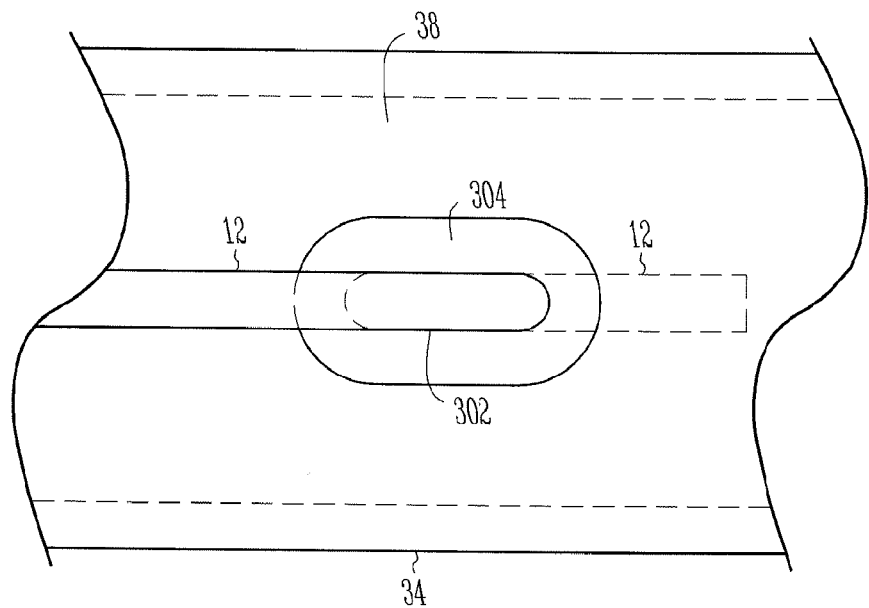
FIG. 3B is a top view of one example of an interface between the agent delivery tube and the delivery lumen.

As shown in FIGS. 3A and 3B, the delivery tube 12 extends through the delivery interface port 302 and into the delivery lumen 38 to provide fluid communication between the delivery tube and the delivery lumen. The delivery tube 12, in one example, is sealed with the delivery lumen 38 using a delivery seal 304. For instance, an adhesive or the like is positioned at the interface port 302 and provides a fluid tight seal to ensure the agent fluid delivered through the delivery lumen 38 is conducted through the delivery tube 12 to the well 54.

Referring again to FIGS. 1C and 3A, the delivery tube 12 extends along the exterior balloon surface 64 including the shoulder 52 and the well portion 72. For instance, as shown in FIGS. 1C and 3A, the delivery tube 12 extends over top of the exterior balloon surface 64. In another example (not shown), the delivery tube 12 extends along the exterior balloon surface 64 on an inner side of the balloon 14 and the agent delivery orifice 70 opens through the exterior balloon surface 64. Referring now to FIG. 3A, the delivery tube 12 is configured to wrap along the balloon and follows the undulating surface of the balloon 14 including the proximal shoulder 52 (having a tapered portion and a separate elevated portion adjacent the well portion 72) and the well portion 72. In one example, the delivery tube 12 is constructed integrally with the balloon 14 and thereby is compliant to deploy with the balloon 14 from the stored configuration shown in FIG. 1B. In another example, the delivery tube 12 is coupled with the balloon 14 (e.g., with adhesives, heat bonding and the like) and is relatively compliant to deform with deployment of the balloon 14. As previously discussed herein, during deployment, the proximal shoulder 52 provides a seal (through compliance of one or more of the balloon 14, the tube 12 or incorporation of the delivery tube into the balloon wall) around the delivery tube 12 that substantially prevents leakage of the agent fluid from the well 54 during deployment of the balloon 14. In one example, the delivery tube 12 is thereby configured to operate to deliver agent fluid to the well 54 according to any one or more of these mechanisms (incorporation of the delivery tube 12 into the balloon sidewall, compliance of materials) without the fluid leaking around the tube 12.

As shown in FIG. 3A, the delivery tube 12, part of the agent delivery assembly 102 is entirely isolated from the inflatable balloon assembly 100. Each uses separate lumens and features to ensure the agent fluid is not used with the balloon 14 for inflation. Instead, the agent delivery assembly 102 is a dedicated system coupled with the inflatable balloon assembly 100 that cooperates with the inflatable balloon assembly to direct agent fluid into the well 54 for intimate and sealed contact with a designated portion of the vessel wall upon inflation of the balloon 14.

The delivery assembly 102 provides a mechanism to deliver the agent fluid to the well 54 formed by the balloon 14 without otherwise using the agent fluid to inflate or maintain the balloon 14 in the inflated deployed configuration. Instead, the delivery assembly 102 is operated independently to ensure precise measured delivery of a dose of the agent fluid. The delivery assembly 102 cooperates with the occlusions provided by the inflatable balloon assembly 100 (e.g., at the proximal and distal shoulders 52 and 53) to retain the dose of the agent fluid in intimate proximate contact with a designated portion of the vessel wall without dilution of the specified concentration of the agent fluid through mixing with fluids within the vessel. The separation of the delivery assembly 102 from the inflatable balloon assembly 100 ensures that the desired inflation pressure is maintained in the balloon 14 without otherwise requiring weeping of the agent through weep holes as in other balloons. Further, filling of the relatively large volume of the inflatable balloon 14 (relative to the well 54) is similarly avoided. Instead, a small volume of the agent fluid fills the space of the well 54 (e.g., between the shoulders 52 and 53, the well portion 72 and the vessel wall). Discarding of agent fluid, such as an expensive therapeutic fluid, used only for inflation of the relatively large volume of the balloon 14, but not otherwise administered is thereby avoided.

Optionally, the inflatable balloon 14 has a plurality of spacing projections 56, including, but not limited to, raised portions, bumps, spirals and the like that aid in delivery or maintaining the well in another example. See FIG. 1C. As shown, the spacing projections 56 extend outwardly from the surface of the well portion 72. The plurality of spacing projections 56 space the well portion 72 from an interior surface of a vessel wall while the balloon 14 is in the deployed configuration shown in FIG. 1C and the shoulders 52 and 53 are similarly engaged with the vessel wall. The spacing projections 56 thereby space the vessel wall from the well portion 72 and facilitate the delivery of the agent fluid to the entirety of the well 54 and the overlying vessel wall during administration of the agent fluid into the well 54. As described below in another example, the spacing projections 56, provide mechanical stimulation, abrasion and the like to the vessel wall (e.g., during one or more of inflation and ongoing engagement after inflation) to ensure intimate contact between the vessel wall and the agent fluid administered to the well 54 from the delivery tube 12.

In one example, the spacing projections 56 are integrally formed with the balloon 14. For instance, the spacing projections 56 are co-molded with the balloon 14. In another example, the spacing projections are applied to the balloon 14, such as with adhesive and the like.

In other embodiments, the balloon catheter 10 may be used with other devices, such as, for example and without limitation, balloon expandable stents. In the example of a balloon expandable stent, the delivery tube 12 infuses the therapeutic or other solution at the stent site. In another example, the balloon catheter 10 may deliver a stent and then bathe the site with a therapeutic or other liquid solution. Optionally, the balloon catheter 10 with the balloon 14, as described herein, is used in an angioplasty procedure and may supply agent fluids to the treated vessel (e.g., between the shoulders 52 and 53) at one or more of before, after and during the angioplasty procedure. As discussed herein, the agent fluid is supplied to the well 54 at a separate controlled pressure relative to the inflation pressure of the balloon 14.

Methods of using the balloon catheter 10 are also embodied herein. In one embodiment, the balloon catheter 10 is advanced to the site or location requiring treatment. The balloon 14 is inflated, followed by infusion of the therapeutic agent through the delivery tube 12 at the treatment site. The balloon 14 may remain inflated for a period of time to ensure adequate delivery. After treatment, the balloon 14 is deflated and the catheter 10 may be either relocated to another location requiring treatment with the same or different therapeutic agent or the catheter 10 may be removed from the patient.

The balloon catheter 10 as disclosed herein may be used in multiple locations with multiple therapeutic agents in various concentrations. In addition, an exact and known amount of therapeutic agent may be accurately delivered. As such, patient treatment may be optimized.

EXAMPLE

The following discussion illustrates non-limiting examples of embodiments of the present disclosure.

A balloon catheter having an external delivery tube as disclosed herein was constructed by carving back the delivery lumen before a balloon was bonded to the other lumens or the catheter shaft. A polypropylene tube having about a 0.014 inch outer diameter, about a 0.010 inch inner diameter, and about a 1.0 inch length was bonded into the delivery lumen by bonding the tip of the tube to the balloon and bonding of the delivery tube proximal to the delivery orifice along evenly spaced locations, for example three locations, until the tube was secured into the delivery lumen. Bonding of the delivery tube to the balloon occurred via methods as known in the art such as through the use of adhesives, heat bonding, welding and the like.

The balloon catheter having an external delivery tube disclosed herein was used in a chronic porcine stenosis study. The catheter was used to deliver 3 mg/cc of paclitaxel to a target site in a porcine blood vessel. The 24 hour tissue concentration was 2.70 μg/ml.

The agent delivery catheter is shown in FIGS. 1A-C transitioning from a stored configuration to a deployed configuration. The agent delivery catheter 10 is shown in a stored configuration in FIG. 1B. The agent delivery catheter 10 is in a deployed configuration in FIGS. 1A and 1C. Referring first to FIG. 1B, the agent delivery catheter 10 is shown with the balloon 14 in a stored or wrapped configuration along the catheter shaft 16. As shown, the balloon 14 is deflated and has a substantially or near substantially isodiametric perimeter (e.g., a stored perimeter) relative to the catheter shaft 16. In the stored configuration, the agent delivery catheter 10 including the catheter shaft 16 and the inflatable balloon 14 are navigated through vasculature to deliver the balloon 14 (as well as the delivery tube 12 extending along the balloon 14) to a designated portion of the vasculature, for instance, a vessel wall designated for treatment with an agent fluid delivered by the delivery tube 12. After the agent delivery catheter 10 is navigated through the vasculature so the balloon 14 and the delivery tube 12 are positioned where desired within the vessel, inflation fluid is delivered through the inflation lumen 36 to the balloon 14 to inflate the balloon 14 into the deployed configuration shown in FIGS. 1A and 1C (as well as FIG. 3A).

Referring to FIGS. 1C and 3A, the balloon 14 is shown in the deployed configuration with the proximal and distal shoulders 52 and 53 positioned adjacent to the well portion 72 thereby forming the well 54 between the shoulders 52 and 53. As previously discussed, the inflation of the balloon 14 engages the shoulders 52 and 53 with the vessel wall and thereby substantially closes the well 54 to prevent the leakage of agent fluids delivered, for instance by the delivery tube 12 to the well 54. The proximal and distal shoulders 52 and 53 have shoulder perimeters greater than a stored perimeter of the balloon 14 in the stored configuration shown in FIG. 1B.

Referring now to FIG. 3A, the agent delivery catheter 10 is again shown in the deployed configuration. For instance, the proximal balloon end 66 is shown in a deployed configuration with the shoulder 52 elevated relative to the well portion 72. The well 54 is thereby formed between the shoulders 52 and 53 (see the distal shoulder 53 shown in FIG. 1C). The well portion 72 is recessed relative to the proximal and distal shoulders 52 and 53 to provide an agent recess or well 54 therebetween. As previously discussed, the delivery tube 12 extends over the exterior balloon surface 64 to provide an agent delivery orifice 70 within the well 74. As shown in FIG. 3A, the delivery tube 12 extends along the exterior balloon surface 64, for instance, closely following the undulating surface of shoulder 52 and the well portion 72. As shown in FIG. 3A, the delivery tube 12 closely follows the curves and bends of the exterior balloon surface 64 thereby positioning the agent delivery orifice 70 within the well 54.

In one example, the balloon 14 is constructed with a first polymer material capable of inflation from the stored configuration shown in FIG. 1B to the deployed configuration shown in FIGS. 1A, C. For instance, the balloon 14 is constructed with, but not limited to, PET, Dacron, nylon composites, polyethylene-nylon composite, Pebax® resin, latex, silicone, and the like. The balloon 14 is constructed with these materials to be compliant, semi-compliant or non-compliant with regard to stretching of the balloon 14 material during inflation. Optionally, the balloon 14 is constructed with a first material and the catheter shaft 16 is constructed with a different material. As shown in FIG. 3A, in one example, the balloon 14 material is gripped between the catheter shaft 16 and the marker bands 50 to fix the balloon 14 to the catheter shaft 16. In another example, the balloon 14 is coupled with the catheter shaft with one or more of welding, adhesives, mechanical fittings and the like.

After deployment of the balloon 14 into the deployed configuration shown in FIGS. 1A, 1C and 3A, the well 54 is provided in close proximity to the vessel wall. Agent fluid, (e.g., a therapeutic agent) is delivered through the delivery lumen 38 and thereafter into the delivery tube 12. The agent fluid is administered to the designated portion of the vessel through the at least one agent delivery orifice 70 of the delivery tube 12. As previously discussed in one example, one or more of the delivery tube 12 and the shoulder 52 are sufficiently compliant to ensure a fluid tight seal or near fluid tight seal is created around the delivery tube 12 at its interface between the vessel wall and the shoulder 52. Delivery of the agent fluid into the well 54 through the agent delivery orifice 70 administers the agent into close intimate contact with the vessel wall immediately proximate to the well portions 72. As shown in FIG. 3A, because the well 54 is provided in close proximity to the vessel wall the relatively small dose of agent fluid delivered through the delivery tube 12 is administered around the well 54, for instance, circumscribing the balloon 14 at the well portion 72. The agent fluid thereby readily engages in intimate contact with the corresponding portion of the vessel wall overlying the well portion 72.

With the above described configuration, delivery of the agent fluid, for instance, into the inflatable balloon 14 and thereafter administering the agent fluid through weep holes within the inflatable balloon 14 is not required. Stated another way, inflating the inflatable balloon 14 (with agent fluid) having a larger volume relative to the well 54 defined between the shoulders 52 and 53 and the well portions 72 is avoided. Instead, with the agent delivery catheter 10 the agent fluid is delivered by itself in an isolated manner from the inflatable balloon 14 through the delivery tube 12 to the well 54. Precise metering of a specified dose of agent fluid having a specified concentration is thereby facilitated without having to manage the inflation pressure of the inflatable balloon 14 and the agent fluid. The agent delivery assembly 102 including the delivery tube 12, the delivery lumen 38 and the delivery channel 24 are entirely separated from the inflatable balloon assembly 100 including the inflatable balloon 14, the inflation lumen 36 and the inflation channel 20. That is to say, the inflatable balloon assembly 100 cooperates with the agent delivery assembly 102. For instance, the inflatable balloon assembly 100 inflates the balloon to provide the well 54 configured to receive the agent fluid therein. After inflation of the balloon 14, the agent delivery assembly 102 (entirely separate from the inflatable balloon assembly 100) delivers the agent fluid through the delivery tube 12 into the well 54. The agent fluid is retained within the well 54 through occluding engagement of the shoulders 52 and 53 of the inflated balloon 14 with the vessel wall.

Figure 4:
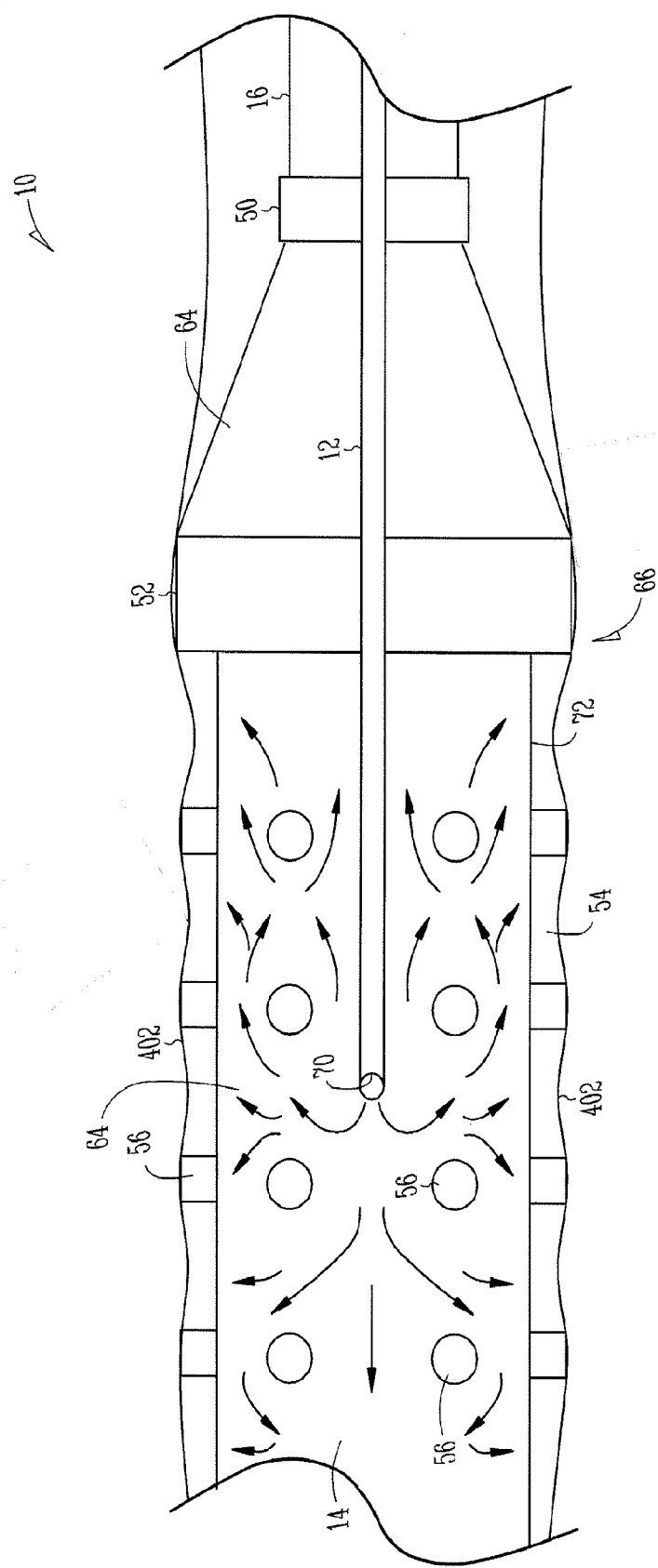
FIG. 4 is a detailed side view of the inflatable balloon shown in FIG. 1C in the deployed configuration with agent fluid flowing through a well and around spacing features formed on the well portion surface.

Referring now to FIG. 4, the agent delivery catheter 10 is shown in a deployed configuration. The balloon 14 includes a plurality of the spacing features 56 (e.g., spacing projections) previously shown and described in FIG. 1C. As shown in FIG. 4, the deployed agent delivery catheter 10 is in an expanded configuration with the balloon 14 engaged with a vessel wall 402. The plurality of arrows directed along the exterior balloon surface 64 of the balloon 14 show the agent fluid being delivered through the agent delivery orifice 70 of the delivery tube 12 and through the well 54. The spacing projections 56 are shown engaged with the vessel wall 402 and space the vessel wall 402 away from the exterior balloon surface 64. Spacing of the vessel wall 402 from the exterior balloon surface 64 ensures the well 54 extends from the proximal shoulder 52 to the distal shoulder 53. Stated another way, the vessel wall 402 is not permitted to lay against any substantial portion of the exterior balloon surface 64. Instead, as agent fluid is delivered through the delivery tube 12 the fluid is able to distribute across the entirety of the well portion 72 thereby ensuring intimate contact between the agent fluid and the vessel wall occurs between the proximal and distal shoulders 52 and 53.

In another example, the spacing projections 56 engage with and mechanically stimulate the vessel wall 402 upon deployment of the balloon 14 from the stored configuration to the deployed configuration shown in FIG. 4. In still another example, the spacing projection 56 engage with and mechanically stimulate the vessel wall 402 while the balloon 14 is maintained in the deployed configuration shown in FIG. 4 where the plurality of spacing projections 56 are engaged along the vessel wall 402. Optionally, engagement of the spacing projections 56 with the vessel wall 402 includes mechanical stimulation of the vessel wall 402, for instance, minor abrasions of the vessel wall to ensure the agent fluid delivered through the delivery tube 12 is able to engage in close intimate contact with the tissues of the vessel.

FIGS. 5A and 5B show another example of an agent delivery catheter 500. The agent delivery catheter 500 is similar in at least some regards to the agent delivery catheter 10 previously shown in FIGS. 1A-D. For instance, the agent delivery catheter 500 includes a catheter shaft 16 extending distally to a balloon 14. The balloon 14 is shown in FIG. 5A in a stored configuration and in a deployed configuration in FIG. 5B. Referring again to FIG. 5A, the balloon 14 includes proximal and distal shoulders 52 and 53 and an intervening portion therebetween configured to form a well 54 as described below. Additionally, a stem portion 47 extends through the balloon 14 to a tip 48. The stem portion 47, in one example, includes a guidewire lumen 40 extending therethrough. Additionally, the agent delivery catheter 500 includes a delivery tube 12 extending along the exterior balloon surface 64 (further described in FIG. 5B). The delivery tube 12 is in communication with a delivery lumen 38 as shown in FIG. 5A. In a similar manner, the inflatable balloon 14 is in communication with an inflation lumen 36. Optionally, the inflation lumen 36, the delivery lumen 38 and the guidewire lumen 40 are incorporated into a trilumen shaft, such as the trilumen tube 34 previously described herein.

Referring now to FIG. 5B, the agent delivery catheter 500 is shown with the balloon 14 in a deployed configuration. As shown the inflatable balloon 14 is inflated and the proximal and distal shoulders 52 and 53 extend away from the remainder of the balloon 14 including the well portion 72. The shoulders 52 and 53 in combination with the well portion 72 form the well 54 therebetween. Additionally, the delivery tube 12 extends along the exterior balloon surface 64, for instance, over the proximal shoulder and into the well 54. As shown in FIG. 5B, the delivery tube 12 extends along the well portion 72 and presents at least one delivery orifice 70 positioned within the well 54. In still further embodiments (not shown), the delivery tube 12 of any of the embodiments disclosed herein, can have multiple delivery orifices in order to deliver the liquid agent at various points within well 54 at the same time. This can be accomplished through perforations in the delivery tube 12 itself or through a forked delivery tube that has multiple arms each having its own delivery orifice at its end. As shown in FIG. 5B, the balloon 14 of the agent delivery catheter 500 does not include the spacing projections 56 previously shown in FIGS. 1C and 4. Instead, the well portion 72 is a substantially uniform surface interposed between the proximal and distal shoulders 52 and 53. In one example, agent fluid is delivered through the delivery tube 12 into the well 54 with sufficient pressure to distribute the agent fluid across the well portion 72 and thereby substantially ensure the entirety or near entirety of a vessel wall overlying the well 54 is intimately contacted with the agent fluid. Stated another way, the spacing projections 56 are an optional feature and the recessing of the well portion 72 from the elevated shoulders 52 and 53 substantially ensures the delivery of agent fluid throughout the well 54 for intimate engagement with the vessel wall overlying the well 54 of the balloon 14. In operation, the agent delivery catheter 500 shown in FIGS. 5A, 5B operates in a substantially similar manner to the agent delivery catheter 10 shown in FIGS. 1A-D. For instance, inflation fluid is delivered to the inflatable balloon 14 through the inflatable balloon assembly 100 to engage the shoulders 52 and 53 with the vessel wall and thereby close the well 54. After deployment of the inflatable balloon 14 into the configuration shown in FIG. 5B, the agent delivery assembly 102 is operated to deliver agent fluid through the delivery lumen 38 and thereafter into the delivery tube 12 for administration of the fluid into the well 54. Delivery of the agent fluid into the well 54 ensures intimate contact of a relatively small volume (e.g., a precise dose having a specified concentration) with the corresponding portion of the vessel overlying the well 54. The proximal and distal shoulders 52 and 53 seal along the vessel wall and thereby ensure the agent fluid is retained within the well 54 according to the requirements of the procedure (e.g., a desired residence time, concentration, and volume of the agent fluid).

Figure 6A:
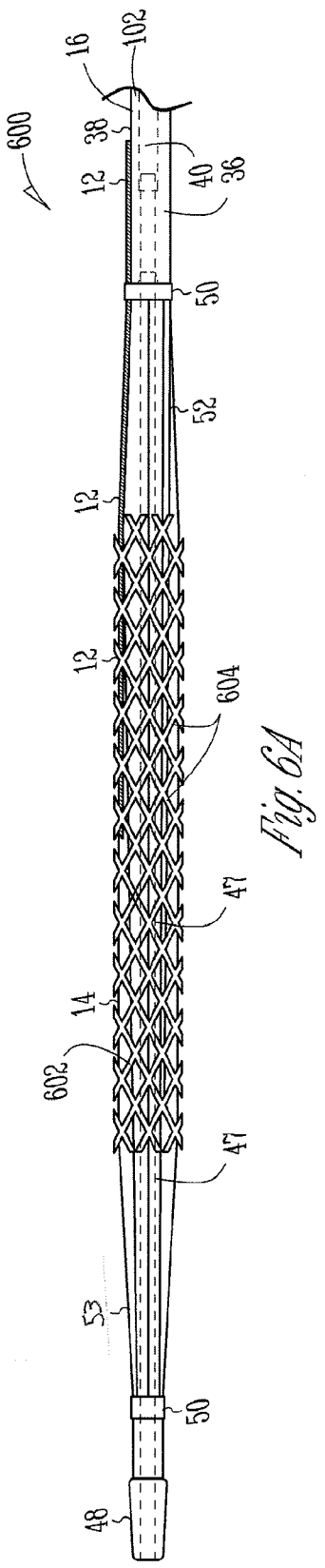
FIG. 6A is a detailed side view of another example of an agent delivery catheter with an expandable cage, such as a fixed cage or deployable stent, positioned around an inflatable balloon in a stored configuration.
Figure 6B:
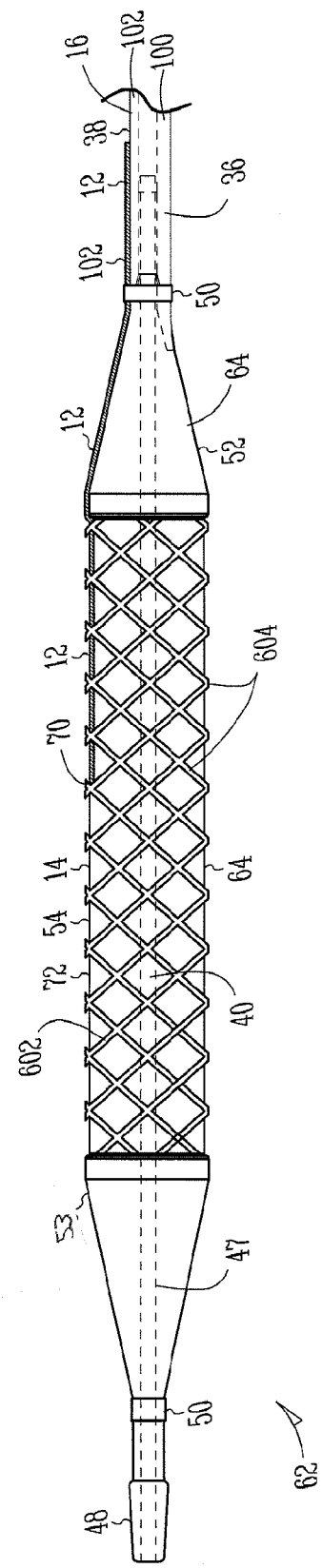
FIG. 6B is a detailed side view of the agent delivery catheter of FIG. 6A showing the inflatable balloon and the expandable cage (a fixed cage or deployable stent) in deployed configurations with a delivery tube interposed therebetween.

FIGS. 6A and 6B show another example of an agent delivery catheter 600 including a cage 602 formed from a plurality of struts 604 coupled with the inflatable balloon 14. FIG. 6A shows the agent delivery catheter 600, for instance, the inflatable balloon 14 and the cage 602 in a stored configuration. FIG. 6B shows the inflatable balloon 14 and the cage 602 in a deployed configuration. Referring first to FIG. 6A, the cage 602 is shown in a stored configuration surrounding the inflatable balloon 14. For instance, the cage 602 in one example, is positioned between the proximal and distal shoulders 52 and 53. The cage 602 is constructed with a plurality of struts 604 configured to facilitate expansion of the cage 602 into the deployed configuration shown in FIG. 6B. In one example, the cage 602 is a stent configured for deployment and detachment from the inflatable balloon 14. That is to say, the cage 602 is a stent configured for detachable implantation into a vessel upon deployment of the inflatable balloon 14 as shown in FIG. 6B. In another example, the cage 602 is fixably coupled with the agent delivery catheter 600 and correspondingly expands and contracts according to the inflation and deflation of the inflatable balloon 14.

Referring again to FIGS. 6A and 6B, the agent delivery catheter 600 includes in a similar manner to the previously described catheters 10 and 500 an agent delivery assembly 102. As shown, the agent delivery system 102 includes a delivery tube 12 in fluid communication with a delivery lumen 38. The delivery tube 12 extends along the exterior balloon surface 64 and into the well 54 formed between the proximal and distal shoulders 52 and 53 and the well portions 72. The delivery tube 12 is interposed between the cage 602 and the inflatable balloon 14. In one example, during deployment the delivery tube 12 maintains an open configuration to facilitate the delivery of agent fluid through the delivery tube 12 to the agent delivery orifice 70. For instance, one or more of the inflatable balloon 14 and the cage 602 includes a recess therein configured to receive a portion of the delivery tube 12, for instance, at the interface between the shoulder 52 and the cage 602. The recess allows the delivery tube 12 to navigate through the cage 602 and maintain an open configuration for delivery of agent fluid.

In another example, the delivery tube 12 is occluded during expansion of the cage 602, for instance, through inflation of the inflatable balloon 14. After engagement of the cage 602 with the vessel wall, for instance to abrade and thereby mechanically stimulate the vessel wall, the delivery tube 12 is not operated. After mechanical stimulation of the vessel wall the inflatable balloon 14 is at least partially deflated to provide tolerance between the cage 602 and the balloon 14 to thereby open the delivery tube 12 for delivery of agent fluid through the delivery orifice 70. In one example, the inflatable balloon 14 is retained in a substantially inflated configuration (e.g., less than the expanded configuration used to deploy the cage 602) to ensure sealing engagement of the shoulders 52 and 53 with the vessel wall while agent fluid is delivered through the delivery orifice 70 of the delivery tube 12. That is to say, the inflatable balloon is partially deflated to open the delivery tube 12 for passage of the agent fluid to the at least one agent delivery orifice 70.

Referring now to FIG. 6B, the cage 602 is shown in detail coupled between the shoulders 52 and 53. In one example, the shoulders 52 and 53 provide bracketing engagement to fix the cage 602 therebetween. In one example, the agent delivery catheter 600 is reciprocated during deployment to ensure engagement of the plurality of struts 604 with the tissue of the vessel wall. The plurality of struts 604 correspondingly abrade at least a portion of the vessel wall to ensure intimate contact between the tissues of the vessel wall and the agent fluid delivered into the well 54 by the delivery tube 12. In still another example, the deployment of the inflatable balloon 14 (e.g., its expansion) engages the plurality of struts 604 with the tissues of the vessel wall and stimulates the tissue of the vessel wall to ensure intimate contact between the agent fluid delivered to the well 54. Stated another way, reciprocation of the agent delivery catheter 600 is not required in this example. Instead, the engagement of the plurality of struts 604 of the cage 602 with the vessel wall mechanically stimulates the vessel tissues and facilitates intimate contact between the agent fluid and the vessel wall.

In one example, the plurality of struts 604 include but are not limited to nitinol, stainless steel, cobalt chromium alloys, polymers, composites and the like. The plurality of struts 604 are interconnected at various juncture points in a manner similar to stent construction. For instance, upon inflation of the inflatable balloon 14 the plurality of struts 604 move from a collapsed configuration shown, for instance, in FIG. 6A to the more expanded configuration shown in FIG. 6B. For instance, the pitch of the plurality of struts 604 increases relative to the configuration of the struts 604 shown in FIG. 6A.

In operation, the agent delivery catheter 600 is navigated through vasculature in a manner similar to the previously described agent delivery catheters 10 and 500. Upon delivery of the inflatable balloon 14 including the cage 602 thereon to a desired location within the vasculature the inflatable balloon 14 is operated. For instance, the inflatable balloon assembly 100 (separate from the agent delivery assembly 102) delivers inflation fluid to the inflatable balloon 14 and deploys the inflatable balloon 14 into the configuration shown in FIG. 6B.

For instance, the proximal and distal shoulders 52 and 53 are expanded into a configuration where the shoulders are engaged with the vessel and thereby provide a sealing engagement therebetween. The well portion 72 is recessed relative to the shoulders 52 and 53 and forms a well 54 therein. In a similar manner, the cage 602 is expanded into the configuration shown in FIG. 6B. As previously described, expansion (or in another option reciprocation) of the cage 602 engages the plurality of struts 604 with the tissues of the vessel wall and thereby mechanically stimulates the same.

In one example, where a recess for the delivery tube 12 is provided in one or more of the cage 602 or the exterior balloon surface 64 the delivery tube 12 is maintained in an open configuration during expansion of the inflatable balloon 14 and the cage 602. Agent fluid is thereafter delivered through the delivery tube 12 to the well 54. As with previous examples, the agent fluid delivered to the well 54 is in close and intimate contact with the vessel wall overlying the well 54. In another example, the cage 602 is expanded and the delivery tube 12 is occluded in the expanded configuration shown, for instance, in FIG. 6B. The pressure within the inflatable balloon is thereafter decreased a small amount to maintain the sealing engagement of the shoulders 52 and 53 with the vessel wall while at the same time opening the delivery tube 12. Agent fluid is thereafter delivered through the delivery tube 12 into the well 54 formed between the shoulders 52 and 53 and the well portion 72.

In still another example, the inflatable balloon 14 is partially inflated into a substantially deployed configuration where the plurality of shoulders 52 and 53 engage with the vessel wall. In this configuration, the cage 602 is not fully deployed and tight engagement between the cage 602 and the inflatable balloon is not yet realized. In this configuration the delivery tube 12 is retained in an open configuration. Agent fluid is thereafter delivered through the agent delivery orifice 70 into the well 54. After delivery of the agent fluid into the well 54 the pressure within the inflatable balloon (separate from any pressure used to deliver the agent fluid through the delivery tube 12) is increased to further expand the inflatable balloon 14. Increased expansion of the inflatable balloon correspondingly expands the cage 602 and engages the plurality of struts 604 with the vessel walls previously described. In this example, the additional expansion of the cage 602 squeezes the delivery tube 12 and occludes the delivery tube. However, the agent fluid has been previously delivered to the well 54 and occlusion of the delivery tube 12 does not otherwise frustrate the intimate contact of the agent fluid with the vessel wall. As discussed herein, the agent fluid is delivered to the vessel at one or more times before, after or during a procedure (e.g., to form the well 54 and/or conduct an angioplasty dilation of the vessel).

In the example including the cage 602 as a deployable component of the agent delivery catheter 600 the cage 602 remains coupled with the catheter (e.g., the balloon 14) throughout navigation, deployment and removal of the catheter 600. For instance, the cage 602 is constructed with a shape memory material and heat set according to the stored (folded) configuration of the balloon 14, as shown in FIG. 6A. After expansion of the balloon 14 and the cage 602 (shown in FIG. 6B) the cage 602 collapses back into the stored configuration having a smaller profile according to its heat setting and is removed with the catheter 600.

In the example including the cage 602 as a deployable stent of the agent delivery catheter 600, the cage 602 is a stent that is implanted within the vessel through inflation and expansion of the balloon 14. For instance a protective sheath is placed around the catheter 600 including the cage 602 during navigation. The sheath is withdrawn after the balloon 14 and the cage 602 (e.g., stent) are delivered to the desired portion of the vasculature. Inflation of the balloon 14 correspondingly expands and deploys the cage 602 for implantation in the vessel. In one example, the cage 602 includes shape memory materials and is heat set in a configuration corresponding to the diameter of the vessel (e.g., the cage 602 is biased into the deployed configuration). After inflation, the cage 602 remains in the deployed state and engaged with the vessel wall according to the previously described heat setting. The balloon 14 is deflated and stored and the catheter 600 is then withdrawn from the vessel leaving the cage 602 implanted as a stent.

Figure 7:
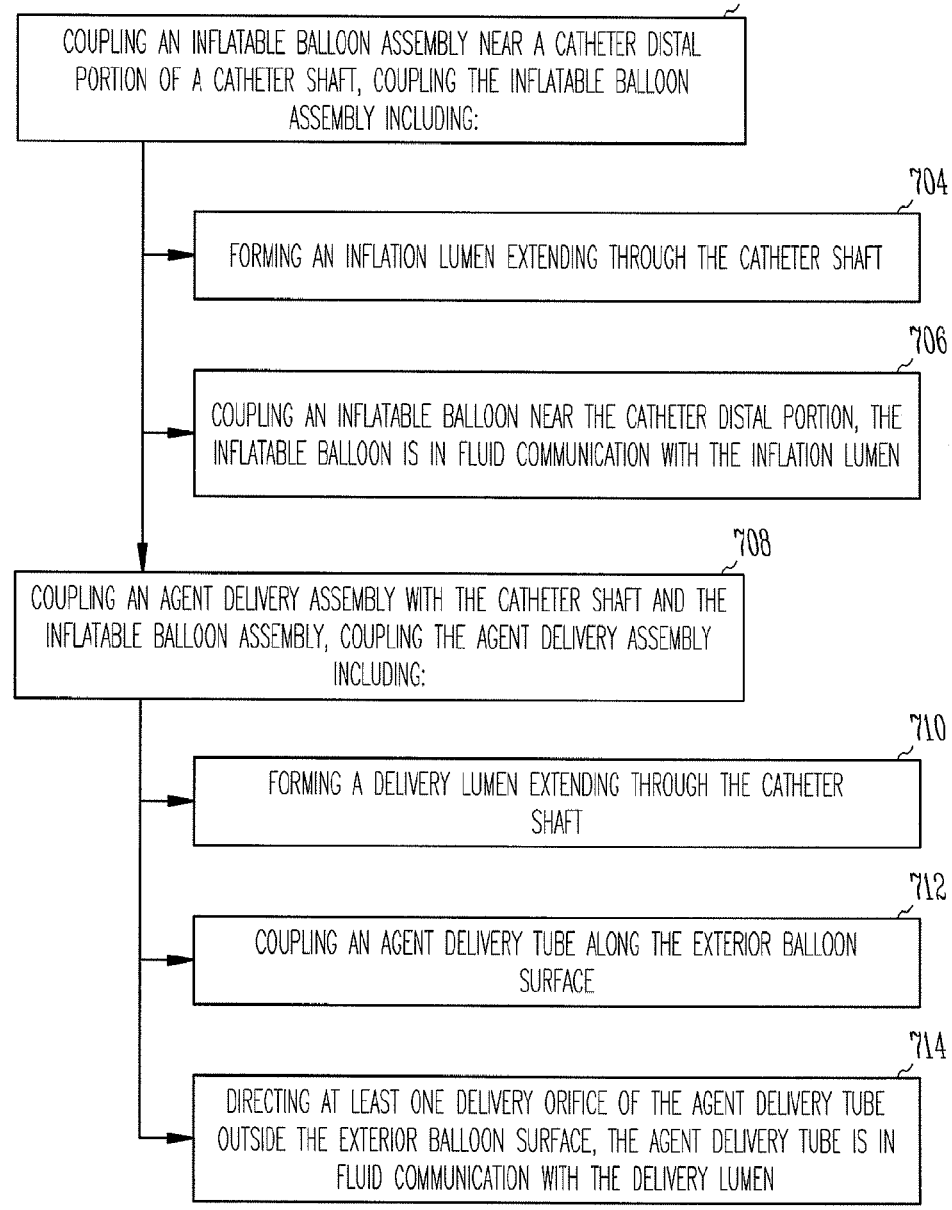
FIG. 7 is a block diagram showing one example of a method for making an agent delivery catheter.

FIG. 7 shows one example of a method 700 for making an agent delivery catheter such as the agent delivery catheters 10, 500 and 600 previously described herein. In describing the method 700 reference is made to features and elements previously described herein. Where appropriate reference numbers are included. The reference numbers are not intended to be limiting. Instead, features and elements described in the method 700 should be accorded a broad interpretation based on similar features described herein as well as their equivalents.

At 702, an inflatable balloon assembly 100 is coupled near a catheter distal portion 62 of a catheter body (e.g., a catheter shaft 16 optionally including a manifold assembly 18). Coupling the inflatable balloon assembly 100 includes, in one example, forming an inflation lumen 36 extending through the catheter body, at 704. In another example, coupling the inflatable balloon assembly 100 near the catheter distal portion 62 includes coupling an inflatable balloon 14 near the catheter distal portion 62, at 706. The inflatable balloon 14 is in fluid communication with the inflation lumen 36. In another example, coupling the inflatable balloon 14 near the catheter distal portion 62 includes coupling the inflatable balloon 14 around at least a portion of the catheter body. For instance, the inflatable balloon 14 is wrapped around the stem portion 47 of a trilumen tube 34 including the inflation lumen 36, a delivery lumen 38 and a guidewire lumen 40. As shown in FIG. 1C, the inflatable balloon is wrapped around the guidewire lumen 40.

At 708, an agent delivery assembly 102 is coupled with the catheter body (e.g., the catheter shaft 16) and the inflatable balloon assembly 100. Coupling the agent delivery assembly 102 includes, in one example, forming a delivery lumen 38 extending through the catheter body, at 710. Coupling the agent delivery assembly 102 with the catheter body includes coupling the agent delivery tube 12 along the exterior balloon surface 64, at 712. In one example, coupling the agent delivery tube 12 along the exterior balloon surface 64 includes positioning the agent delivery tube 12 outside the inflatable balloon 14 from the interface with the delivery lumen 38 (e.g., at the deliver interface port 302) to the at least one delivery orifice 70. At 714, at least one delivery orifice 70 of the agent delivery tube 12 is directed outside of the exterior balloon surface (e.g., into the well 54). As described herein, the agent delivery tube 12 is in fluid communication with the delivery lumen 38.

Several options for the method 700 follow. In one example, the method 700 includes forming the inflatable balloon with a proximal and distal shoulders 52 and 53. In another example, the proximal and distal shoulders 52 and 53 each include a shoulder perimeter. In another example, forming the inflatable balloon 14 includes interposing a well portion 72 between the proximal and distal shoulders 52 and 53. The well portion 72 includes a well perimeter less than the shoulder perimeter. For instance, as previously described herein the well portion 72 is recessed relative to the proximal and distal shoulders 52 and 53 to form the well 54. In another example, forming the inflatable balloon 14 includes forming a plurality of spacing features 56 (e.g., spacing projections) extending outwardly from the well portion 72 (e.g., a well portion surface). The plurality of spacing features 56 are configured to space the well portion 72 from a vessel interior surface while the plurality of spacing features 56 are engaged with the vessel interior surface. In still another example, forming the inflatable balloon 14 includes forming a well between the proximal and distal shoulders 52 and 53 and the well portion 72. In still another example, directing the at least one delivery orifice outside of the exterior balloon surface includes positioning the delivery orifice 70 along the well portion 72 so the delivery orifice opens into the well 54.

In yet another example, the method 700 includes coupling an expandable structural cage 602 with the agent delivery catheter 600. The structural cage 602 includes a plurality of struts 604 extending around the inflatable balloon 14 (see FIG. 6B). In one example, at least a portion of agent delivery tube 12 is interposed between the structural cage 602 and the inflatable balloon 14. As previously described herein, the agent delivery tube 12 is constructed with but not limited to pliable materials that allow for the deflection of the agent delivery tube during expansion and engagement of the inflatable balloon 14 with the expandable structural cage 600 for deployment of the same. Optionally, one or more of the expandable structural cage 602 and the inflatable balloon 14 include recesses configured to allow free passage of the agent delivery tube 12 therethrough. The agent delivery tube 12 is thereby able to remain in an open configuration even during expansion of the expandable structural cage by inflation of the inflatable balloon 14.

Figure 8:
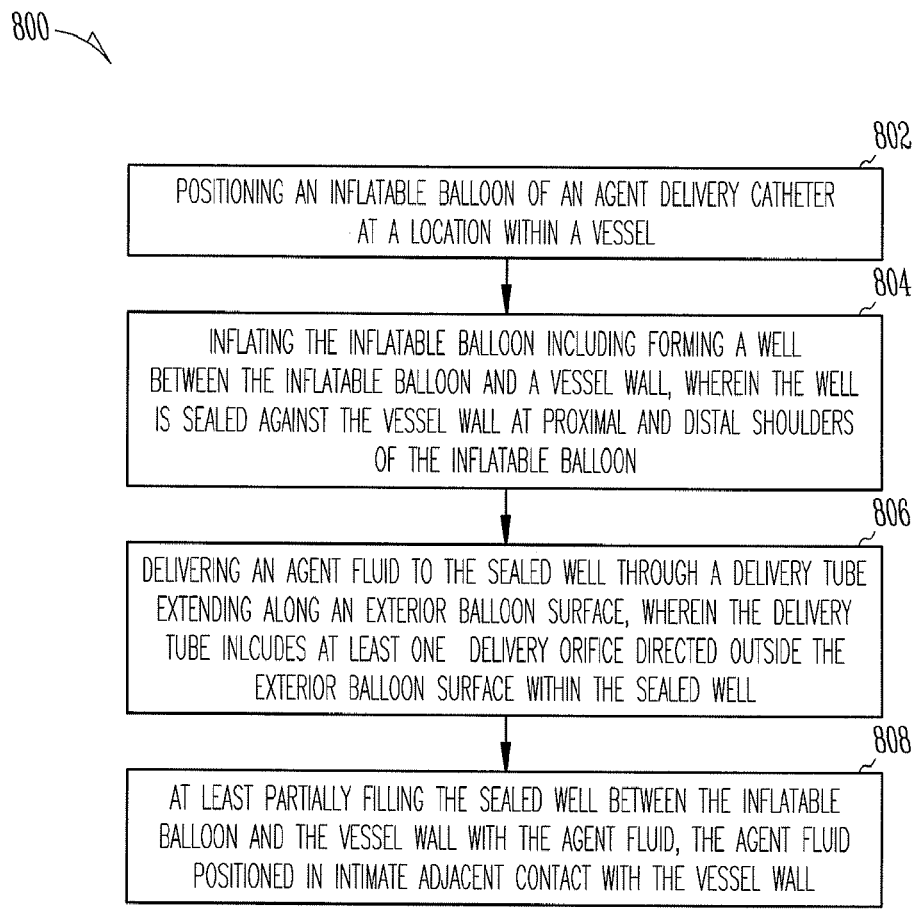
FIG. 8 is a block diagram showing one example of a method for using an agent delivery catheter.

FIG. 8 is a diagram showing one example of a method 800 for using an agent delivery catheter such as the agent delivery catheters 10, 500 and 600 described herein. In the description of the method 800, reference is made to features and elements previously described herein. Where possible reference numbers are included corresponding to previously described features and elements. The reference numbers provided are not intended to be limiting and are instead exemplary. The elements recited in the method correspond to all features similar to the elements described as well as their equivalents. At 802, the method 800 includes positioning an inflatable balloon 14 of an agent delivery catheter 10 at a location within a vessel. For instance, the agent delivery catheter 10 is navigated through the vasculature to a desired portion of the vessel, for instance a portion of the vessel requiring treatment with therapeutic agents delivered through the delivery tube 12 as described herein. At 804, the inflatable balloon 14 is inflated. Inflation of the inflatable balloon 14 forms a well 54 (e.g., an agent recess or pocket) between the inflatable lumen 14 and a vessel wall 402. The well 54 is sealed against the vessel wall 402 at proximal and distal shoulders 52 and 53 of the inflatable balloon 14. Stated another way, inflation of the inflatable balloon (e.g., incorporated into the inflatable balloon assembly 100) deploys the balloon and engages the proximal and distal shoulders 52 and 53 against the vessel wall 402. Engagement of the proximal and distal shoulders 52 and 53 with the vessel wall 402 substantially closes the well 54 and forms a pocket for reception of agent fluid delivered by the agent delivery assembly 102.

At 806, an agent fluid is delivered to the sealed well 54 through a delivery tube 12 extending along an exterior balloon surface 64. The delivery tube 12 includes at least one delivery orifice 70 directed outside the exterior balloon surface 64 within the well 54. For instance, in one example the delivery tube 12 extends along the outer surface of the exterior balloon surface 64 from a delivery interface port 302 to the one or more agent delivery orifices 70. In still another example, the delivery tube 12 extends along the interior of the exterior balloon surface 64 within the balloon 14. The agent delivery orifice 70 extends out of the balloon 14 by penetrating the exterior balloon surface 64 in the well portion 72. At 808, the method 800 further includes at least partially filling the well between the inflatable balloon 14 and the vessel wall 402 with the agent fluid. The agent fluid is positioned in intimate adjacent contact with the vessel wall 402 according to the positioning of the well adjacent to the vessel wall. Stated another way the well portion 72 and the proximal and distal shoulders 52 and 53 cooperate to position the well 54 in close adjacent proximity to the vessel wall 402. Subsequent delivery of the agent fluid through the delivery assembly 102 thereby correspondingly delivers the agent fluid into close intimate contact with the surrounding vessel wall 402 overlying the well portion 72.

Several options for the method 800 follow. In one example, a cage 602 is provided around the balloon 14. Inflating the inflatable balloon expands the cage 602 into a deployed configuration, as shown in FIG. 6B. The agent fluid is delivered to the well after expansion of the cage and relaxation of an inflation pressure of the inflatable balloon, in another example. Stated another way, the shoulders 52 and 53 remain engaged with the vessel wall while the balloon 14 is relaxed to allow opening of the agent delivery tube 12 for delivery of agent fluid to the well 54. Alternatively, one or more of the inflatable balloon and the cage 602 include recesses or openings configured to receive the agent delivery tube 12 and thereby maintain the tube in an open configuration even during full inflation of the balloon and expansion of the cage 602. In still another example, the method includes delivering agent fluid into the well 54 through the agent delivery tube 12 prior to full deployment of the cage 602. For instance, the inflatable balloon is expanded to engage the shoulders 52 and 53 with the vessel wall while the balloon is not sufficiently inflated to tightly engage the cage 602 for expansion of the same. Instead, the agent delivery tube 12 is retained therebetween in an open configuration that facilitates the delivery of the agent fluid until full expansion of the cage 602 is desired.

The agent delivery catheters described herein and the methods for using the same provide systems and methods including an inflatable balloon having a well in close proximity to a specified portion of a vessel wall. The agent delivery catheters further include separate agent delivery assemblies that are fluidly isolated from the inflatable balloon assemblies configured to inflate the balloons. Stated another way, the agent delivery catheters described herein provide dedicated agent fluid delivery systems configured to deliver therapeutic agents to a specified portion of a vessel. The agent delivery assemblies cooperate with the inflatable balloon assemblies to reliably retain the agent fluid in a desired location for a desired residence time. As previously described herein, the inflatable balloon assembly includes, in one example, inflation channels, lumens and the inflatable balloon configured to inflate and provide a well sized and shaped to receive the agent fluid therein. The inflatable balloon assembly provides the well in close proximity to vessel wall designated for treatment. Agent delivery catheters further include the agent delivery assemblies including the delivery channel, the delivery lumen and the delivery tube extending into the well. By providing separate and dedicated inflatable balloon assemblies and agent delivery assemblies the agent delivery catheters described herein provide dilation with the balloon entirely separate from the infusion function of the agent delivery assemblies. Further, the agent delivery assemblies include delivery tubes extending along the exterior balloon surface and configured to deliver the agent fluid into the well formed by the inflatable balloon.

The inflatable balloon assemblies described herein facilitate precise maintenance of the inflation and dilation of the inflatable balloon throughout operation of the agent delivery catheters. The inflatable balloon reliably retains the agent fluid at the desired location for the desired residence time. Stated another way, the inflatable balloon provides the well according to the inflated configuration of the shoulders and the well portion of the inflatable balloon. Constant maintenance and delivery of inflation fluid to a balloon including weeping holes configured to infuse fluid to the surrounding tissue is thereby avoided. Stated another way, the inflatable balloon assembly is a closed system that does not include drug infusion lumens.

The agent delivery assembly facilitates precise metering of the agent fluid (e.g., a therapeutic agent) into the well formed by the inflatable balloon. That is to say, a precise dose of a therapeutic agent with a specified concentration is administered to the well according to the operation of the agent delivery assembly separate from the inflatable balloon assembly. The provision of a fluidly separate agent delivery assembly avoids the unpredictability of weep holes provided in an inflatable balloon that are otherwise used to infuse therapeutic agents to surrounding tissue. The deformability of the weep holes frustrates the ability to precisely meter a specified dose and specified concentration of the therapeutic agent to the desired tissue.

As described herein, the agent delivery assembly administers the agent fluid into the well provided by inflation of the balloon and thereby substantially ensures the delivery of the agent fluid to the vessel wall overlying the well. The inflated balloon substantially ensures that the agent delivered into the well is in close intimate contact according to the inflation and positioning of the proximal and distal shoulders and the well portion substantially adjacent to the vessel wall. Further, the inflated balloon retains the agent at a desired location with substantially no leakage downstream. Because the inflatable balloon assembly and the agent delivery assembly are separate from each other the inflatable balloon is filled with an inflation fluid that is entirely separate from the therapeutic agent used in the agent delivery assembly. Stated another way, the therapeutic agent fluid is delivered in relatively small volumes to the well formed adjacent to the vessel wall while a relatively large volume of inflation fluid (e.g., a less expensive fluid, such as saline) is delivered to the inflatable balloon having a correspondingly larger volume. Efficient and economical use of the therapeutic agent is thereby realized.

The present disclosure has been described with reference to specific details of particular embodiments thereof. It is not intended that such details be regarded as limitations upon the scope of the disclosure except insofar as and to the extent that they are included in the accompanying claims.

Benefits, other advantages and solutions to problems have been described above with regard to particular examples; however, any benefit, advantage, solution to problems or any element that may cause any particular benefit, advantage or solution to occur or to become more pronounced are not to be construed as critical, required or essential features or components.

As used herein, the terms "comprises", "comprising", or any variation thereof, are intended to reference a non-exclusive inclusion, such that a process, method, article, composition or apparatus that comprises a list of elements does not include only those elements recited, but may also include other elements not expressly listed or inherent to such process, method, article, composition or apparatus. Other combinations and/or modifications of the above-described structures, arrangements, applications, proportions, elements, materials or components used in the practice of the present subject matter, in addition to those not specifically recited, may be varied or otherwise particularly adapted to specific environments, manufacturing specifications, design parameters or other operating requirements without departing from the general principles of the same.

The present subject matter has been described above with reference to examples. However, changes and modifications may be made to the examples without departing from the scope of the present subject matter. These and other changes or modifications are intended to be included within the scope of the present subject matter, as expressed in the following claims.

It is to be understood that the above description is intended to be illustrative, and not restrictive. Many other examples will be apparent to those of skill in the art upon reading and understanding the above description. It should be noted that examples discussed in different portions of the description or referred to in different drawings can be combined to form additional examples of the present application. The scope of the subject matter should, therefore, be determined with reference to the appended claims, along with the full scope of equivalents to which such claims are entitled.

What is claimed is:

1. An agent delivery catheter comprising:

a catheter body extending from a catheter proximal portion to a catheter distal portion, the catheter body including an inflation lumen and a delivery lumen, each lumen extending from the catheter proximal portion toward the catheter distal portion;

an inflatable balloon coupled near the catheter distal portion, the inflatable balloon in fluid communication with the inflation lumen and extending around at least a portion of the catheter body, the inflatable balloon including:

an exterior balloon surface, a proximal and a distal shoulder portion, and a well portion between the proximal and distal shoulder portions; and an agent delivery tube extending along the exterior balloon surface, the agent delivery tube including at least one delivery orifice positioned outside of the exterior balloon surface and adjacent to the well portion, the agent delivery tube in fluid communication with the delivery lumen;

wherein the inflatable balloon is configured for dilation from a stored configuration to a deployed configuration such that:

in the stored configuration the inflatable balloon has a stored perimeter, and in the deployed configuration the proximal and distal shoulder portions each have a shoulder perimeter greater than the stored perimeter and the well portion has a well perimeter recessed relative to the shoulder perimeter, wherein the at least one delivery orifice opens into a volume between the proximal and distal shoulder portions and the well portion;

wherein the inflatable balloon contains a first volume of inflation fluid in the deployed configuration, and the at least one delivery orifice is configured to deliver a second volume of agent fluid, wherein the second volume of agent fluid is less than the first volume of inflation fluid.

2. The agent delivery catheter of claim 1, wherein the inflation lumen and the inflatable balloon are fluidly separated from the delivery lumen and the agent delivery tube.

3. The agent delivery catheter of claim 1, wherein the second volume of agent fluid at least partially fills the volume between the proximal and distal shoulder portions and the well portion.

4. The agent delivery catheter of claim 1, wherein the well portion includes a plurality of spacing projections extending outwardly from a well portion surface, the plurality of spacing projections configured to space the well portion surface from a vessel interior surface while the plurality of spacing projections are engaged with the vessel interior surface when the inflatable balloon is in the deployed configuration.

5. The agent delivery catheter of claim 1, wherein the agent delivery tube is outside of the inflatable balloon from the delivery lumen to the at least one delivery orifice.

6. The agent delivery catheter of claim 1, wherein a delivery seal is provided at an interface between the agent delivery tube and the delivery lumen on the catheter body.

* * * * *